US011584697B2

(12) United States Patent
Klein

(10) Patent No.: US 11,584,697 B2
(45) Date of Patent: Feb. 21, 2023

(54) METHOD FOR THE PRODUCTION OF ORGANIC FERTILIZER BASED ON AMMONIUM AND/OR NITRATE

(71) Applicants: Klein Holding B.V., RW Roelofarendsveen (NL); Petrus Franciscus Klein, RW Roelofarendsveen (NL)

(72) Inventor: Petrus Franciscus Klein, RW Roelofarendsveen (NL)

(73) Assignee: KLEIN HOLDING B.V., Roelofarendsveen (NL)

( * ) Notice: Subject to any disclaimer, the term of this patent is extended or adjusted under 35 U.S.C. 154(b) by 472 days.

(21) Appl. No.: 16/627,092

(22) PCT Filed: Jul. 4, 2018

(86) PCT No.: PCT/NL2018/000014
§ 371 (c)(1),
(2) Date: Dec. 27, 2019

(87) PCT Pub. No.: WO2019/009699
PCT Pub. Date: Jan. 10, 2019

(65) Prior Publication Data
US 2020/0140346 A1    May 7, 2020

(30) Foreign Application Priority Data
Jul. 4, 2017    (NL) ...................... 1042451

(51) Int. Cl.
C05C 1/00    (2006.01)
C12N 1/16    (2006.01)
C12P 3/00    (2006.01)
(52) U.S. Cl.
CPC .................. C05C 1/00 (2013.01); C12N 1/16 (2013.01); C12P 3/00 (2013.01)

(58) Field of Classification Search
CPC ..... C05C 1/00; C12N 1/16; C12P 3/00; C02F 2101/16; C02F 2209/06; C02F 2209/22; C02F 2301/046; C02F 3/302
See application file for complete search history.

(56) References Cited

U.S. PATENT DOCUMENTS 4,720,344 A     1/1988   Ganczarczyk et al.
2008/0156726 A1 7/2008   Fassbender

FOREIGN PATENT DOCUMENTS

CN    104496100 B  *  7/2016    ............... C02F 9/10
DE    3332710 A1   *  3/1985    ............... A01C 3/02
(Continued)

OTHER PUBLICATIONS

United States Environmental Protection Agency, Nitrification, Office of Water, Office of Ground Water and Drinking Water, Distribution System Issue Paper (Aug. 15, 2002). (Year: 2002).*

(Continued)

Primary Examiner — Jennifer A Smith
(74) Attorney, Agent, or Firm — Tarolli, Sundheim, Covell & Tummino LLP

(57) ABSTRACT

Method for the production of organic fertilizer comprising providing an organic source of ammonia gas, in particular air contaminated with ammonia gas, directing the air contaminated with ammonia gas through water and forming an ammonium hydroxide solution converting the ammonium into nitrate, dosing, under the control of a control system, the ammonium hydroxide solution to a recirculation stream from a second bio-reactor with bacteria suitable for converting the supplied ammonia into nitrite and nitrate. The amount of ammonium water fed by the control system to the acidic nitrate solution from the second bio-reactor depends on one or more measured pH values in the device.

6 Claims, 1 Drawing Sheet

(56) References Cited

FOREIGN PATENT DOCUMENTS

| JP | 2011240254 | A | | 12/2011 | |
|----|------------|---|---|---------|---|
| WO | 0005176 | A1 | | 2/2000 | |
| WO | 2005113455 | A1 | | 12/2005 | |
| WO | WO-2007097612 | A2 | * | 8/2007 | .......... C05F 17/0018 |
| WO | WO-2009046415 | A1 | * | 4/2009 | .............. C02F 3/006 |

OTHER PUBLICATIONS

Machine translation of CN-104496100-B (Year: 2016).*
Machine translation of DE-3332710-A1 (Year: 1985).*
International Search Report for International Application No. PCT/NL2018/000014 dated Feb. 27, 2019.

* cited by examiner

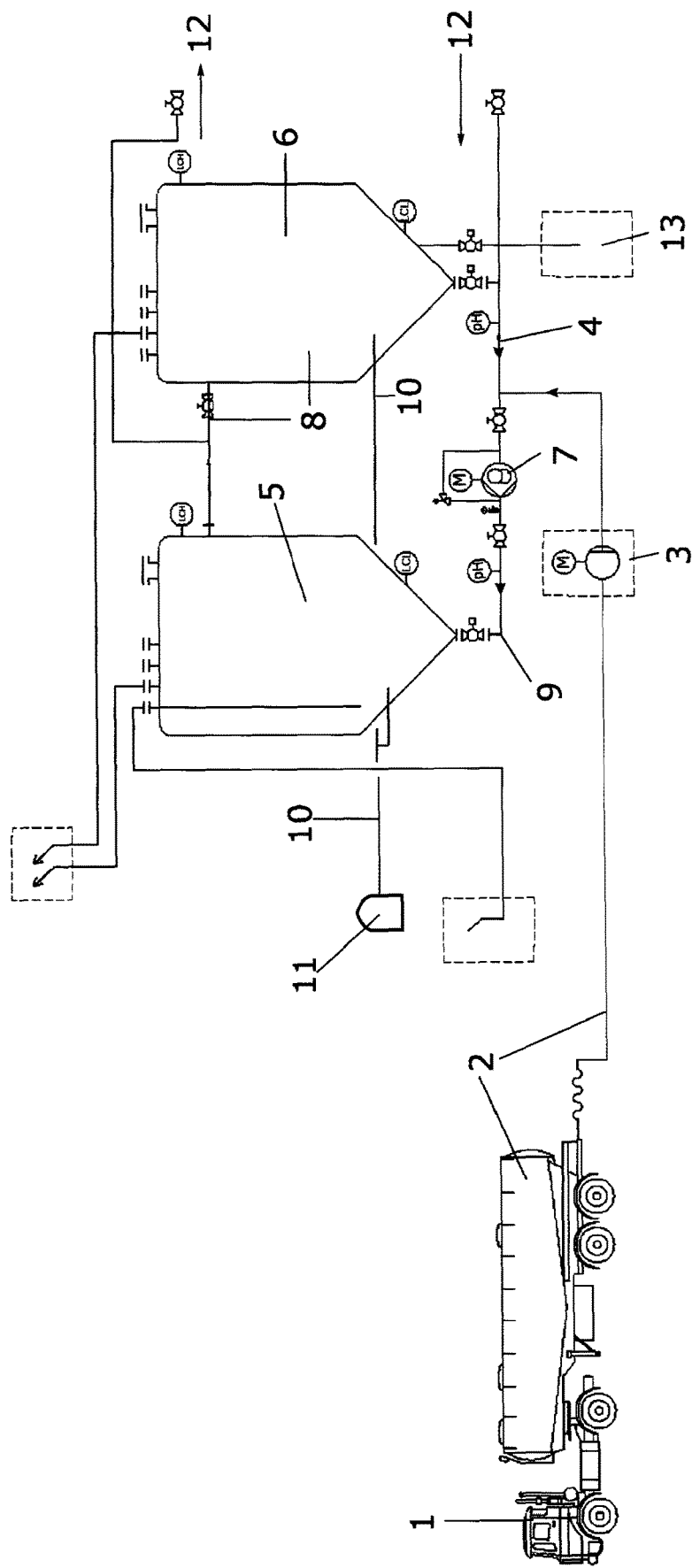

METHOD FOR THE PRODUCTION OF ORGANIC FERTILIZER BASED ON AMMONIUM AND/OR NITRATE

RELATED APPLICATIONS

The present invention is a U.S. National Stage under 35 USC 371 patent application, claiming priority to Serial No. PCT/NL2018/000014, filed on 4 Jul. 2018; which claims priority of NL 1042451, filed on 4 Jul. 2017, the entirety of both of which are incorporated herein by reference.

The invention relates to a method for the production of, inter alia, organic fertilizer based on ammonium and/or nitrate.

Crops (see, among others https://www1.agric.gov.ab.ca/$department/deptdocs.nsf/all/agdex3791) take up nitrogen (N) predominantly in the form of nitrate ($NO_3^-$) or ammonium ($NH_4+$). Therefore, conventional fertilizers contain one of these or both forms, or compounds as urea which are converted into ammonium and then into nitrate fairly quickly. Nitrate is quickly absorbed by the plant but is mobile in the soil and therefore easily rinses out. Under wet conditions due to denitrification, $N_2O$ emissions from nitrate-containing fertilizers are considerably higher than from ammonium or urea-based fertilizers. Ammonium can also be absorbed by the plant, but for a large part the ammonium is firstly converted into nitrate by micro-organisms in the soil, which makes the absorption process slower. Because of the positive charge, the ammonium is readily absorbed by organic matter and clay particles of the soil and rinses out less easily. However, there is a certain risk of ammonia volatilization, especially with acidic soil. Firstly, urea in the soil must be converted into ammonium which could result in volatilization but reduces the risk of rinsing out. Ammonium and nitrate-based fertilizers, such as Ammonium Nitrate or AN and Calcium Ammonium Nitrate or CAN, provide the highest N-utilization and N-absorption and the lowest $NH_3$ emission, but have the highest $N_2O$ emission and nitrate leaching under wet conditions. Therefore, in the early spring it is advisable to opt for fertilizers with a higher ammonium content. An additional advantage is that especially at lower temperatures plants have a preference for N-absorption in the form of ammonium. Additionally, ammonium stimulates the absorption of phosphate.

Particularly, the hereabove described fertilizer is applicable in agriculture. In horticulture, almost all drainage water is recirculated. This means that nitrate is not leaking to the groundwater. The object of the present invention is to provide a system and method for the production of organic fertilizer based on ammonium and/or nitrate, which fertilizer, produced in this way, is particularly useful in horticulture, but also in agriculture and in particular in the organic horticulture and organic agriculture respectively.

In composting of chicken and pig manure, in purification of contaminated water, in roasting of coffee and other processes, ammonia gas is released. The ammonia can be removed from the ambient air by means of a (gas, wet) scrubber, in which the ammonia gas is absorbed in a scrubbing liquid by passing the contaminated air with ammonia gas through a vessel with water, thereby dissolving the ammonia gas in the water and converting the ammonia into ammonium hydroxide (see also https://nl.wikipedia.org/wiki/Luchtwasser). In order to ensure that the process runs smoothly, it is important that organic dust particles are removed by filtering from the air stream contaminated with ammonia gas, which is supplied to the water scrubber, so that the quality of the water and the active bacteria therein are not reduced by these organic dust particles.

After ammonia gas has been converted to ammonium, the ammonium remains in the water scrubber. The air coming out of the water scrubber is almost completely purified from the (polluting) ammonia gas.

By continuously pumping ammonia gas through the water, the ammonium concentration in the water increases. Ammonium can be converted to nitrate by dosing/pumping the ammonium water, under the control of a control system, from the water tank of the air scrubber to a bio-reactor (also called nitrification vessel) containing ammonia-oxidizing bacteria and nitrite-oxidizing bacteria, including *Nitrobacter* bacteria, which convert the ammonium in the bio-reactor into nitrate. During the oxidation of ammonium nitrate to nitrite and nitrate (nitric acid) acid is formed and the pH of the solution will drop sharply. At a pH lower than 6, the ammonia-oxidizing bacteria and nitrite-oxidizing bacteria are no longer active. Therefore, according to the invention, a second bio-reactor with a recirculation is provided, which collects the acidic nitrate solution from the first bio-reactor. Because the nitrate concentration is too low after one pass through the first bio-reactor, the acidic nitrate solution from the second bio-reactor is recirculated to the first bio-reactor by means of a recirculation pump. Into this acidic nitrate solution recirculation stream an amount of $NH_3$ solution in water (ammonium water) is added, so that in the feed stream to the first bio-reactor simultaneously the pH increases to six and above together with an increase of the concentration of the nitrogen compounds, $NH_3$, $NH_4^+$, $NO_2$, $NO_3^-$. By means of a control system and pH meters, the (measured) pH value of the liquid in the first bio-reactor is kept constant at an optimal value for the bacteria. The optimal desired pH value ("Sollwert") is preferably in the range 4.5-8.5, and more preferably in the range 6.5-7.3. The optimal desired pH value is maintained by the control system by measuring the pH in the second bio-reactor or in the acidic nitrate solution recirculation stream ("Istwert") and by determining and controlling the quantity of ammonium to be supplied to the bio-reactor dependent on the optimal desired pH value and the measured pH value of the liquid in the first bio-reactor.

A feedback loop may be provided by measuring the pH of the feed stream of the first bio-reactor, which is a mixture of the dosed $NH_3$ solution in water and the acidic nitrate solution recirculation flow from the second bio-reactor.

It is noted that besides the bacterium *Nitrobacter*, more bacterial strains may be needed, such as *Nitrosomonas*. In order to improve the efficiency, bacteria can also be used to support the *Nitrobacter* and/or *Nitrosomonas* bacteria, such as a number of bacilli, collectively called nitrifying bacteria. Nitrogen-fixing bacteria can also be used that absorb nitrogen from the air and reduce the nitrogen that escapes during the process.

Preferably, the first bio-reactor and optionally the second bio-reactor are provided with an aeration unit and oxygen meters by means of which the control system can maintain the oxygen concentration of the liquid within the reactors. Preferably, the first bio-reactor comprises surface expanders on which the bacteria can grow. It is important that the feed stream, for instance by means of mixing baffles in the first bio-reactor, is forced to flow through the entire reactor before it flows out from the discharge location of the first bio-reactor to the second bio-reactor.

The nitrification process is a constant process in which the feed stream is controlled by the control system based on the measured pH value. The ammonia contained in the $NH_3$ solution in water, that is dosed to the first bio-reactor, leaves the first bio-reactor at its discharge location as an acidic nitrate solution.

The nitrate coming from the first bio-reactor can be highly concentrated at, for example, a maximum of 25%, by means of prolonged repeated recirculation over the second bio-reactor. Or the nitrate may be aimed at a low concentration of, for example, about 1% by applying a low recirculation ratio. At low concentrations, the nitrate can be removed from the liquid by means of filtration (for example by nanofiltration) and separated from any remaining ammonium. The remaining liquid (water) can be reused again. The final product can be stabilized by killing the bacteria, for example by heating to a minimum of 63° C.

$H^+$ ions are formed during the process. They reduce the pH of the product. The product also stabilizes in an acidic environment (pH <7). Stabilization of the final product can thus be effected, not only by killing the bacteria, but also by lowering the pH, as has been shown by tests. Preferably, this acid neutralization is performed by adding $NH_3$ solution in water, whereby ammonium nitrate is formed.

The quality/authenticity (organic/non-organic) of the nitrate obtained can be demonstrated by measuring the isotope values. Organic nitrate is a young fertilizer and therefore contains Nitrogen-15 isotopes while a chemical nitrate has predominantly Nitrogen-14 isotopes. The authenticity of the end product can thus be demonstrated as organic nitrate.

The organic ammonium as well as the organic nitrate can thus be produced from ammonia gases originating from animal or vegetable residual streams, but also from ammonia gases originating from, for example, water purification plants.

The organic nitrate produced with this method is eminently suitable for use as organic fertilizer in, inter alia, (organic and non-organic) agriculture and horticulture, public green areas, maintenance of sports fields, urban farming, aquaculture (aquaponics), air cultivation (aeroponics), substrate cultivation (hydroponics) and soil-based crop cultivation. For example, the nitrogen that can be extracted from the produced nitrate can also be used for the production of yeasts.

Hereinafter the invention will be discussed in more detail with reference to an embodiment, with reference to a FIGURE.

FIG. 1 shows an embodiment of a device for converting $NH_3$ to nitric acid and/or to ammonium nitrate.

EXAMPLE

FIG. 1 shows a flowchart of a device according to the invention for carrying out the method according to the invention.

In this example, the $NH_3$ to be converted to the bio-nitrate fertilizer is supplied by a tank truck 1 as a $NH_3$ solution in water 2.

The composition of the $NH_3$ solution in water 2 is determined by the following equilibria:

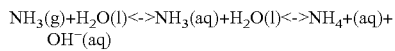

The $NH_3$ solution in water 2 is basic (alkaline) with a pH>7 due to the formation of $OH^-$ during the dissolution of $NH_3$.

By means of a $NH_3$ dosing device 3, the $NH_3$ solution in water 2 is dosed into the recirculation stream 4 from the second bio-reactor 6 to the first bio-reactor 5. The recirculation stream 4 is maintained by a recirculation pump 7. The first bio-reactor 5 is a vessel with preferably a conical bottom in which a mixture is present of some ammonia-oxidizing bacteria including Proteobacteria, *Nitrosomonas* and *Nitrosococcus*. In this example, the second bio-reactor 6 is a vessel of the same size as the first bio-reactor 5. The first and second bio-reactors are aerated with air 10 (or oxygen) from an aerating unit 11 to an $O_2$ saturation of at least 80% at the prevailing temperature. The oxygen concentration in the first and second bio-reactor is measured with oxygen meters.

The liquid content of the first and second bio-reactor 5, 6 is heated to a temperature of approximately 28° C. Under these conditions, the ammonia-oxidizing bacteria will oxidize the ammonium hydroxide with oxygen to nitrite according to the following overall reaction equation.

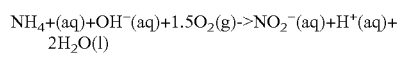

In a second reaction step, the nitrite formed is oxidized with oxygen to nitrate by nitrite-oxidizing bacteria according to the reaction equation:

Oxidation of nitrite to nitrate is carried out by nitrite-oxidizing bacteria including *Nitrobacter* and *Nitrospira*. As a result, the basic (alkaline) feed of $NH_3$ solution in water 2 is converted into an acidic nitrate solution 8 (nitric acid) having a pH <7. This acidic nitrate solution 8 flows to the second bio-reactor 6, where the conversion of nitrite to nitrate further continues, although the pH rises quickly and is often too high for the nitrite-oxidizing bacteria.

Subsequently, the content of the second bio-reactor 6 is recirculated to the first bio-reactor 5 by means of the recirculation stream 4 provided by recirculation pump 7. In this recirculation stream 4 the pH is measured and on the basis of the pH measurement the $NH_3$ dosing device 3 doses a corresponding amount of basic $NH_3$ solution in water 2, so that a pH >7 is obtained with the solution of the formed feed stream 9 and as a result all nitric acid from the second bio-reactor is converted to ammonium nitrate.

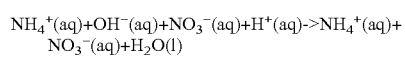

The ammonia-oxidizing bacteria in the first bio-reactor 5 convert the ammonium nitrate to nitrite according to the following overall reaction equation:

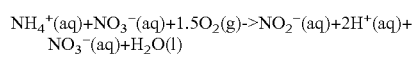

In a second step, the nitrite formed is converted to nitrate according to the reaction equation:

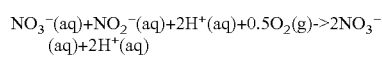

From the above reaction equations, it is clear that the concentration of $HNO_3$ (nitric acid) has doubled in the effluent of the first bio-rector after the first recirculation. Here, for convenience, the small dilution by the water formed is not taken into account in the oxidation of $NH_4^+$ (aq). As a result, the nitrate concentration in the second bio-reactor 6 will increase over time.

During the next recirculation of the second bio-reactor to the first bio-reactor, the concentration of nitrate will increase again. The unit is operated for a predetermined period of time, and the nitric acid/ammonium nitrate mixture in the second bio-reactor is recirculated for a predetermined period of time, resulting in a nitrate concentration of 10 wt. % or more in water. With this method, it is possible to obtain nitrate concentrations in the second bio-rector between 2 and 25% by weight. This product is suitable for use as organic fertilizer or organic raw material.

In a next step, the first bio-reactor 5 and the second bio-reactor 6 are disconnected from each other and optionally the acidic nitrate product in the second bio-reactor is made basic or pH neutral by forming ammonium nitrate with the $NH_3$ solution in water 2 according to the reaction equation:

$$NH_4^+(aq)+OH^-(aq)+NO_3^-(aq)+H^+(aq) \rightarrow NH_4^+(aq)+NO_3^-(aq)+H_2O(l)$$

It is also possible to increase the concentration of nitric acid and/or ammonium nitrate by evaporation or otherwise removing the solvent water.

The nitrate solution in the second bio-reactor 6 is then discharged to the final product filling plant 13 or to, for example, a tank truck for transport to a packaging unit.

When a third bio-reactor 12 is added to the device (unit) for carrying out the method according to the invention, the device can be operated continuously. The third bio-reactor 12 is configured in parallel with the second bio-reactor, so that the acidic nitrate solution 8 can flow from the first bio-reactor 5 to the third bio-reactor 12 and recirculate to the first bio-reactor 5, while the produced nitrate solution in the second bio-reactor 6 is discharged, for example to the final product filling plant 13.

The invention claimed is:

1. Method for the production of organic fertilizer or organic raw material for, inter alia, the manufacture of yeast, based on ammonium and/or nitrate, comprising the steps of:
   providing an organic source of ammonia gas;
   dissolving the ammonia gas in water to form an $NH_3$ solution in water;
   oxidizing ammonium hydroxide in the $NH_3$ solution in water with air to nitrite by means of bacteria, and then oxidizing the nitrite with air to nitrate by means of bacteria to form an acidic nitrate solution,
   characterized, in that the method comprises the steps:
   producing an acidic nitrate solution in a first bio-reactor by means of bacteria;
   discharging the acidic nitrate solution from the first bio-reactor to a second bio-reactor for further conversion of nitrite to nitrate by means of bacteria;
   maintaining an $O_2$ saturation of at least 80% at the prevailing temperature in the first bio-reactor and the second bio-reactor;
   recirculating the content from the second bio-reactor to the first bin-reactor as an acidic nitrate solution recirculation stream;
   wherein an $NH_3$ solution in water is dosed into the acidic nitrate solution recirculation stream to form a feed stream of the first bio-reactor having a greater than 6, said feed stream being supplied to the first bio-reactor, wherein the amount of $NH_3$ solution in water suppled to the acidic nitrate solution recirculation stream is controlled by a control system dependent on the measured pH value of the acidic nitrate solution recycle stream and/or the measured pH value in the feed stream;
   disconnecting the first bio-reactor and the second bin-reactor; and
   discharging the nitrate solution of the second bio-reactor.

2. Method according to claim 1, wherein the acidic nitrate solution from the second bio-reactor is recirculated repeatedly until the nitrate concentration is between 2 and 25% by weight in the second bio-reactor.

3. Method according to claim 1, wherein the desired pH value of the feed stream controlled by the control system is in the range of 6.5-7.3.

4. Method according to claim 1, wherein the $NH_3$ solution in water is fed to the acidic nitrate solution of the second bio-reactor to form an ammonium nitrate solution.

5. Method according to claim 1, wherein the first bio-reactor comprises surface expanders on which allow the bacteria grows.

6. Method according to claim 5, wherein the first bio-reactor comprises mixing baffles being arranged to cause the feed stream, fed to the first bio-reactor, to pass through the first bio-reactor, and flow out form the discharge location of the first bio-reactor.

* * * * *